United States Patent
Priou et al.

(10) Patent No.: US 6,291,540 B1
(45) Date of Patent: Sep. 18, 2001

(54) NON-TOXIC INITIATORS AND THEIR USE FOR PREPARING STABLE AND NON-TOXIC POLYMERS

(75) Inventors: Christian Priou, West Windsor, NJ (US); Jacques Richard, Luzinay (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/402,779

(22) PCT Filed: Apr. 14, 1998

(86) PCT No.: PCT/FR98/00741

§ 371 Date: Mar. 10, 2000

§ 102(e) Date: Mar. 10, 2000

(87) PCT Pub. No.: WO98/46647

PCT Pub. Date: Oct. 22, 1998

(30) Foreign Application Priority Data

Apr. 11, 1997 (FR) .................................. 97/04458

(51) Int. Cl.$^7$ ................ C08F 2/50; G03F 7/029
(52) U.S. Cl. .............. 522/31; 522/99; 522/100; 522/104; 522/148; 522/168; 522/170; 522/181; 522/182; 528/12; 528/13; 528/19; 528/21; 528/23; 528/33; 528/408; 528/421
(58) Field of Search .............. 522/31, 148, 170, 522/99, 181, 182, 108, 100, 104, 168, 25; 528/33, 12, 13, 23, 408, 421, 38, 19, 21

(56) References Cited

U.S. PATENT DOCUMENTS

| | | | |
|---|---|---|---|
| 4,336,366 | * | 6/1982 | Berner et al. . |
| 4,394,403 | * | 7/1983 | Smith . |
| 4,868,092 | * | 9/1989 | Kawabata et al. . |
| 4,882,201 | * | 11/1989 | Crivello et al. . |
| 5,055,439 | * | 10/1991 | Allen et al. . |
| 5,374,500 | * | 12/1994 | Carpenter, Jr. et al. . |
| 5,703,137 | * | 12/1997 | Priou et al. . |
| 5,744,511 | * | 4/1998 | Kazama et al. . |
| 5,773,194 | * | 6/1998 | Hattori et al. . |

FOREIGN PATENT DOCUMENTS

| | | |
|---|---|---|
| 41 10 793 | 4/1992 | (DE) . |
| 2 270 269 | 12/1975 | (FR) . |

* cited by examiner

*Primary Examiner*—Susan W. Berman
(74) *Attorney, Agent, or Firm*—Burns, Doane Swecker & Mathis, L.L.P.

(57) ABSTRACT

The invention concerns a novel method for preparing non-toxic resins crosslinkable under radiation in the presence of an initiator system. Said resins are prepared from compositions of an organic and/or silicon type comprising monomers, oligomers and/or polymers with organofunctional groups, and are cross-linked in the presence of an initiator system consisting of an onium salt with low toxicity whereof the cationic structure is $[(CH(CH_3)_2-C_6H_4-)-I-(-R^1)]+(I)$.

24 Claims, No Drawings

NON-TOXIC INITIATORS AND THEIR USE FOR PREPARING STABLE AND NON-TOXIC POLYMERS

The present invention relates to a novel process for preparing non-toxic resins which can be crosslinked under irradiation in the presence of an initiator system. These resins are prepared from compositions comprising monomers, oligomers and/or polymers containing organofunctional groups, and are crosslinked in the presence of an initiator system consisting of an onium salt of very low toxicity.

The novel resins according to the invention are used for preparing non-toxic inks, non-toxic, non-stick or anti-adhesive coatings and for preparing articles consisting of a solid support, at least one surface of which is made non-stick or anti-adhesive by coating using the said irradiation-crosslinkable resins, in particular by photochemical activation or by activation with a beam of electrons.

Onium salts or salts of organometallic complexes are well known as cationic polymerization photoinitiators for monomers or polymers containing functional groups of epoxide and vinyl ether type. Many documents describe these photoinitiators and their use: U.S. Pat. Nos. 4,069,054; 4,450,360; 4,576,999; 4,640,967; CA 1,274,646; EP-A-203, 829.

However, most of these initiator salts of the prior art are difficult to handle and also present risks of toxicity, which thus limits their field of application, and in particular the use of the crosslinked resins obtained in the presence of these initiators in applications associated with the food industry, such as the wrapping and coating of plastics and metals in particular, for food packaging.

The Applicant has prepared a novel process for preparing resins which are free of risk of toxicity, this process using carefully selected novel initiators which do not have the drawbacks of the prior art, in particular as regards toxicity, thus making it possible to use the said initiators in applications that demand virtually no toxicity. Thus, novel resins have been developed to allow their use in applications associated with the food industry, such as wrapping, and the coating of plastics and metals. These novel resins are prepared from compositions comprising monomers, oligomers and/or polymers containing organofunctional groups, which can be crosslinked under irradiation in the presence of an initiator system; this initiator system is a non-toxic onium salt whose cationic structure is of the formula:

$$[(CH(CH_3)_2\text{-}\Phi\text{-})\text{-}I\text{---}(\text{---}R^1)]^+ \quad (I)$$

in which the symbol $R^1$ represents a radical $-\phi\text{-}R^2$, $R^2$ being a linear or branched alkyl radical comprising from 1 to 20 carbon atoms, preferably 1 to 15 carbon atoms and $\Phi$ respresents a phenyl group.

Preferably, the cationic structure of the onium salt is of the formula $[(CH(CH_3)_2\text{-}\Phi\text{-})\text{-}I\text{-}\Phi\text{-}CH_3]^+$. The reason for this is that the best results have been obtained with this structure, which unites both a very low level of toxicity and optimum activity during the crosslinking of the crosslinkable compositions.

The anionic structure of the onium salt is chosen from the group consisting of $Cl^-$, $Br^-$, $BF_4^-$, $PF_6^-$, $CF_3SO_3^-$, $N(SO_2CF_3)_2^-$, $C(SO_2CF_3)_2^-$, $B(C_6F_5)_4^-$, $B(PhOCF_3)_4^-$, $SbF_6^-$ and/or $AsF_6^-$. However, the following initiators have been found to be particularly suitable in the preparation of non-toxic coatings and/or varnishes:

$[CH_3\text{-}\Phi\text{-}I\text{-}\Phi\text{-}CH(CH_3)_2]^+Cl^-$,
$[CH_3\text{-}\Phi\text{-}I\text{-}\Phi\text{-}CH(CH_3)_2]^+B(C_6F_5)_4^-$,
$[CH_3\text{-}\Phi\text{-}I\text{-}\Phi\text{-}CH(CH_3)_2]^+PF_6^-$, and
$[CH_3\text{-}\Phi\text{-}I\text{-}\Phi\text{-}CH(CH_3)_2]^+B(PhOCF_3)_4^-$.

The crosslinking can be carried out in the presence of various types of irradiation, including heat irradiation. In general, in the context of the presence invention, this crosslinking is carried out under ultraviolet (UV) irradiation and/or under irradiation with an electron beam (E.B.).

Advantageously, the initiators are used in solution in an organic solvent (accelerator), preferably chosen from proton donors and, even more preferably, from the following groups: isopropyl alcohols, benzyl alcohols, diacetone alcohol, butyl lactate and a mixture thereof.

The initiators developed and used in the context of the present invention can be prepared by exchange reaction between a salt of the cationic species, for example a halide (chloride, iodide), a hexafluorophosphate, a tetrafluoroborate or a tosylate with an alkali metal (sodium, lithium or potassium) salt of the anionic species.

The operating conditions, in particular the respective amounts of reagents, the choice of solvents, duration, temperature and stirring, are chosen to allow the initiator according to the invention to be recovered in solid form by filtration of the precipitate formed, or in oily form by extraction with a suitable solvent.

The alkali metal salts of the anionic species can be prepared in a known manner, by exchange reaction between a haloboron compound and an organometallic compound (for example: organomagnesium, organolithium or organotin reagent) bearing the desired hydrocarbon-based groups, in stoichiometric amount, optionally followed by hydrolysis using an aqueous solution of alkali metal halide; this type of synthesis is described, for example, in "J. of Organometallic Chemistry" vol 178, pp. 1–4, 1979; "J.A.C.S" 82, 1960, 5298; "Anal. Chem. Acta" 44, 1969, 175–183; U.S. Pat. No. 4,139,681 and DE-A-2,901,367; "Zh. Org. Khim." Vol.25, No. 5—pages 1099–1102, May 1989.

The tests carried out to measure the toxicity of the initiators are the Ames test and the LLNA sensitization test. The Ames test makes it possible to measure the mutagenic power of the initiator and the LLNA sensitization test makes it possible to detect the sensitizing power of the initiator. The cytotoxicity of the initiators can also be detected in this latter test (see examples).

The monomers and polymers which can be used in the context of the invention for preparing resins from crosslinkable compositions, in accordance with the invention, are very varied in nature. In the context of the invention, the tests were carried out with monomers and polymers of organic nature or of silicone nature.

Among the monomers and polymers of silicone nature, the polymers defined below are used in the context of the invention. These polymers are polyorganosiloxanes containing functional groups of epoxy and/or vinyl ether type.

The said polyorganosiloxanes are linear or substantially linear and consist of units of formula (II) ending with units of formula (III), or are cyclic and consist of units or formula (II) represented below:

(II)

(III)

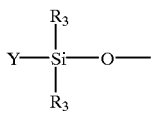

and/or

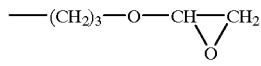        d)

in which the symbols R$_3$ are identical or different and represent:
  a linear or branched alkyl radical containing 1 to 8 carbon atoms, optionally substituted with at least one halogen, preferably fluorine, the alkyl radicals preferably being methyl, ethyl, propyl, octyl and 3,3,3-trifluoropropyl,
  a cycloalkyl radical containing between 5 and 8 carbon atoms, as a ring which is optionally substituted,
  an aryl radical containing between 6 and 12 carbon atoms which may be substituted, preferably phenyl or dichlorophenyl,
  an aralkyl portion with an alkyl portion containing between 5 and 14 carbon atoms and an aryl portion containing between 6 and 12 carbon atoms, optionally substituted on the aryl portion with halogens, alkyls and/or alkoxys containing 1 to 3 carbon atoms, the symbols Y are identical or different and represent:
  the group R$_3$, a hydrogen radical and/or an organofunctional group which can undergo cationic crosslinking, preferably an epoxyfunctional and/or vinyloxyfunctional group linked to the silicon of the polyorganosiloxane via a divalent radical containing from 2 to 20 carbon atoms and which can contain at least one hetero atom, preferably oxygen, and
  at least one of the symbols Y representing an organofunctional group which can undergo cationic crosslinking.

Preferably, at least one of the symbols R$_3$ of the polyorganosiloxanes used in the compositions according to the invention represents a phenyl, tolyl or dichlorophenyl radical.

Furthermore, it is advantageous for at least 60 mol % of the radicals R$_3$ of the polyorganosiloxanes used in the compositions according to the invention to be methyl radicals.

According to one preferred variant of the invention, 1 to 50%, preferably 5 to 25%, of the silicon atoms in the polyorganosiloxane bear one crosslinkable functional group.

By way of example, the epoxyfunctional groups Y are generally chosen from:

a)

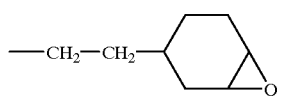

b)

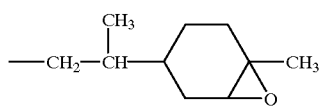

c)

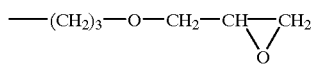

Preferably, the functional groups Y correspond to a).

In addition, the vinyloxyfunctional groups Y are generally chosen from:
  $(CH_2)_3$—O—CH=CH$_2$
  —O—$(CH_2)_4$—O—CH=CH$_2$
  and/or $(CH_2)_3$—O—R$_4$—O—CH=CH$_2$
in which R$_4$ is:
  a linear or branched $C_1$–$C_{12}$ alkylene which may be substituted,
  a $C_5$–$C_{12}$ arylene, preferably phenylene, which may be substituted, preferably with 1 to 3 $C_1$–$C_6$ alkyl groups.

The epoxyfunctional and vinyloxyfunctional polyorganosiloxanes are described in particular in the following references: DE-A-4,009,889; EP-A-396,130; EP-A-335,381; EP-A-105,341; FR-A-2,110,115; FR-A-2,526,800.

The epoxyfunctional polyorganosiloxanes can be prepared by hydrosilylation reaction between oils containing Si—H units and epoxyfunctional compounds such as 1,2-epoxy-4-vinyl-4-cyclohexane or allyl glycidyl ether.

The vinyloxyfunctional polyorganosiloxanes can be prepared by hydrosilylation reaction between oils containing Si—H units and vinyloxyfunctional compounds such as allyl vinyl ether or allylvinyloxy-ethoxybenzene.

The epoxyfunctional or vinyloxyfunctional polyorganosiloxanes are generally in the form of fluids with a viscosity at 25° C. of from 10 to 10,000 mm$^2$/s and preferably from 100 to 600 mm$^2$/s (viscosity measured using a Brookfield viscometer, according to AFNOR standard NFT 76 102 of February 1972).

Among the monomers, oligomers and polymers of organic nature containing organofunctional groups, the polymers and monomers defined below are used in the context of the invention. These monomers, oligomers and polymers comprise epoxy, acrylate, alkenyl ether and/or alcohol reactive functions.

These monomers, oligomers and/or polymers of organic nature belong to at least one of the following species:
  α1.1 cycloaliphatic epoxides, taken alone or as a mixture with each other:
    epoxides of the 3,4-epoxycyclohexyl-methyl 3',4'-epoxycyclohexane-carboxylate type:

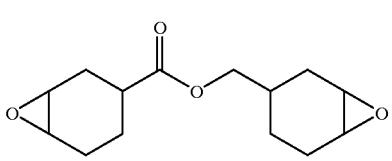

or bis(3,4-epoxycyclohexyl) adipate, being particularly preferred;
  α1.2 non-cycloaliphatic epoxides, taken alone or as a mixture with each other:
    epoxides of the type resulting from the coupling of bisphenol A and epichlorohydrin and of the type:
      triglycidyl ethers of alkoxylated bisphenol A of 1,6-hexanediol, of glycerol, of neopentyl glycol and of trimethylolpropane.
    or bisphenol A diglycidyl ethers, α-olefin epoxides, Novolac epoxides, oxidized soybean oil, epoxidized flax oil and epoxidized polybutadiene, being particularly preferred;

α2 acrylates, taken alone or as a mixture with each other, e.g.:
  epoxidized acrylates, preferably the oligomer bisphenol-A-epoxydiacrylate (Ebecryl 600),
  acrylo-glycero-polyester, preferably the trifunctional acrylate oligomer mixture obtained from glycerol and polyester (Ebecryl 810),
  multifunctional acrylates, preferably pentaerythrityl triacrylate (PETA), trimethylolpropane triacrylate (TMPTA), 1,6-hexanediol diacrylate (HDODA), trimethylolpropane ethoxylate triacrylate, thiodiethylene glycol diacrylate, tetraethylene glycol diacrylate (TTEGDA), tripropylene glycol diacrylate (TRPGDA), triethylene glycol diacrylate (TREGDA) or trimethylpropane trimethacrylate (TMPTMA),
  acrylo-urethanes,
  acrylo-polyethers,
  acrylo-polyesters,
  unsaturated polyesters,
  acrylo-acrylics, being particularly preferred;

α3 linear or cyclic alkenyl ethers, taken alone or as a mixture with each other:
  vinyl ethers, in particular triethylene glycol divinyl ether (Rapidcure® CHVE-3, GAF Chemicals Corp.), cyclic vinyl ethers or acrolein tetramers and/or dimers, and the vinyl ether of the following formula:

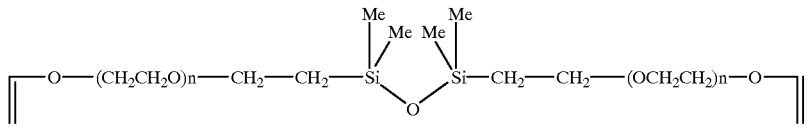

propenyl ethers,
and butenyl ethers being more especially preferred,

α4 polyols, taken alone or as a mixture with each other, and preferably the compound of the formula below:

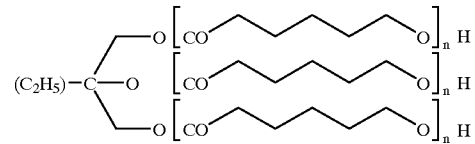

Furthermore, depending on the applications envisaged (for example varnishes), the crosslinkable resins can contain not only momoners, oligomers and/or polymers of organic nature as defined above, but can also contain momoners, oligomers and/or polymers of silicone nature in accordance with the definition given above.

The compositions in accordance with the invention can also comprise other ingredients, such as pigments, adhesion modifiers, photosensitizers for fungicidal, bactericidal and antimicrobial agents, corrosion inhibitors, etc. These compositions can be used in the form provided or in solution in an organic solvent.

The resins of the invention, prepared from compositions comprising monomers, oligomers and/or polymers can be used in many sectors. In particular, non-toxic inks and non-stick, non-toxic coatings are manufactured based on resins according to the invention and are used in the food sector on account of their low toxicity (for example, contact between foods and the inks and/or coatings).

As regards the resins obtained from compositions comprising polyorganosiloxanes, these resins can be used in the sector of non-stick coatings on cellulosic materials, paints, the encapsulation of electrical and electronic components, textile coatings, as well as for sheathing optical fibres. They are most particularly advantageous when they are used in the form provided to make a material, such as metal sheets, glass, plastics or paper, non-stick with respect to other materials to which it would normally adhere. In these sectors of application, resins based on polyorganosiloxanes advantageously have a viscosity not exceeding 5000 mPa·s, preferably not exceeding 4000 mPa·s, at 25° C.

Thus, the crosslinkable compositions based on polyorganosiloxanes make articles (for example sheets) non-stick with respect to surfaces to which they normally adhere. This use is carried out by (a) applying an amount of the composition of the invention, generally between 0.1 and 5 g per $m^2$ of area to be coated, and (b) crosslinking the composition by supplying energy, at least some, preferably all, of which is supplied by UV irradiation.

The UV irradiation used has a wavelength of between 200 and 400 nanometers, preferably between 254 and 360 nanometers. The irradiation time can be short, i.e. less than 1 second and of a few hundredths of a second for low thicknesses of coatings. The crosslinking is carried out in the absence of heating or in the presence of heating to between 25 and 100° C. The curing time is controlled (a) by the number of UV lamps used, (b) by the exposure time to the UV, and/or (c) by the distance between the composition and the UV lamp.

Compositions based on solvent-free polyorganosiloxanes, i.e. undiluted polyorgano-siloxanes, are applied using devices which are suitable for depositing small amounts of liquids uniformly. To this end, the device known as "Helio glissant" comprising in particular two superimposed cylinders, can be used, for example: the role of the cylinder placed at the bottom, dipping into the coating tank containing the composition, is to impregnate the cylinder placed at the top with a very thin layer, and the role of the latter cylinder is then to deposit on the paper the desired amounts of composition with which it is impregnated, such a dosage being obtained by adjusting the respective speed of the two cylinders rotating in opposite directions to one another.

The amounts of compositions deposited on the supports are variable and usually range between 0.1 and 5 $g/m^2$ of area treated. These amounts depend on the nature of the supports and on the non-stick properties desired. They are usually between 0.5 and 1.5 $g/m^2$ for non-porous supports.

A subject of the present invention is also articles (for example sheets) consisting of solid material (metal, glass, plastic, paper, etc.), at least one surface of which is coated with resin of organic nature and/or of silicone nature, as defined above, crosslinked by ultraviolet irradiation or crosslinked by irradiation with an electron beam.

EXAMPLE AND TESTS

The examples and tests below are given for illustrative purposes and cannot be considered as limiting the scope or spirit of the invention.

I. Preparations of Iodonium Salt According to the Invention and According to the Prior Art

Example 1
Synthesis of the Iodonium Salt

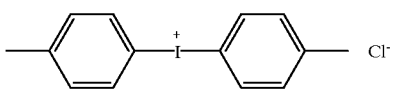

Ice (6.35 g) and sulphuric acid (20 g, 0.2 mol) are placed in a 500 ml four-necked round-bottomed flask fitted with a mechanical stirrer, a dropping funnel, a water-cooled condenser and a thermometer. The mixture is cooled to 20° C. and glacial acetic acid (30 g, 0.5 mol) is then added. Ammonium persulphate (41 g, 0.18 mol) is then added at 20° C.±5° C. The reaction medium is then cooled to 15° C. and stirred at a speed of 420 rpm. Finally, a mixture of 4-iodotoluene (21.8 g; 0.1 mol) in toluene (36.8 g; 0.4 mol) is added over 2 hours, while keeping the temperature at 20° C.

After addition of all the reagents, stirring is continued at 20° C. for 16 to 20 hours, the end of the reaction being determined by TLC (eluent: $CCl_4$). Precipitation of the ditolyliodonium chloride is carried out by addition of an NaCl solution (35 g in 100 ml of water). The mixture is filtered and the yellow precipitate is washed with saturated NaCl a solution and then with water in order to remove the remaining acetic acid. The solid is then washed with toluene, and then with pentane.

After drying in an oven under vacuum, ditolyliodonium chloride is recovered. It is then purified by recrystallization from hot acetone. The yield is 46%.

Analyses: m.p.=188° C.; $^1$H NMR (300 MHz) : δ=2.24 (s, 6H, Me); 7.92 (d, 4H, ArH).

Example 2
Synthesis of the Iodonium Salt

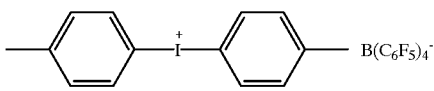

Potassium tetrakis(pentafluorophenyl)borate (14.4 g, 0.02 mol), ditolyliodonium chloride (6.9 g, 0.02 mol) and methanol (90 g) are placed in a 250 ml conical flask fitted with a magnetic stirrer. This mixture is stirred for 1 h at room temperature and then filtered through a No. 4 sinter funnel to remove the potassium chloride formed during the reaction. The solution is taken up in a conical flask fitted with a magnetic stirrer and water (42 g) is then added dropwise over 20 min. The mixture is then kept stirring for 30 min. It is filtered through a No. 4 sinter funnel and the product obtained is then dried for 24 h at 50° C. at a pressure of 18 mm Hg. 16.8 g of a white powder are recovered, equivalent to a yield of 85%.

Analyses: HPLC: Anion 69.6%, cation 28.7%; water content: 0.035%; chloride content: 0.04%.

Example 3
Synthesis of the Iodonium Salt

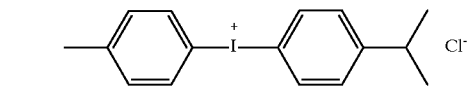

Ice (6.33 g) and sulphuric acid (20.8 g, 0.2 mol) are placed in a 500 ml four-necked round-bottomed flask fitted with a mechanical stirrer, a dropping funnel, a water-cooled condenser and a thermometer. The mixture is cooled to 20° C. and glacial acetic acid (30 g, 0.5 mol) is then added. Ammonium persulphate (41 g, 0.18 mol) is then added at 20° C.±5° C. The reaction medium is then cooled to 15° C. and stirred at a speed of 420 rpm. Finally, a mixture of 4-iodotoluene (21.8 g; 0.1 mol) in cumene (24.42 g; 0.2 mol) is added over 2 hours, while keeping the temperature at 20° C.

After addition of all the reagents, stirring is continued at 20° C. for 16 to 20 hours, the end of the reaction being determined by TLC (eluent: $CCl_4$). Precipitation of the cumyltolyliodonium chloride is carried out by addition of an NaCl solution (35 g in 100 ml of water). The mixture is filtered and the yellow precipitate is washed with a saturated NaCl solution and then with water in order to remove the remaining acetic acid. The solid is then washed with toluene, and then with pentane. After drying in an oven under vacuum, cumyltolyliodonium chloride is recovered. It is then purified by recrystallization from hot acetone. The yield is 75%.

Analyses: m.p.=188.6° C.; $^1$H NMR (300 MHz) : δ=1.09 (d, 6H, Me); 2.24 (s, 3H, Me); δ=2.82 (m, 1H, CH); 7.17 (d, 2H, ArH); δ=7.24 (d, 2H, ArH); 7.94 (dd, 4H, ArH).

Example 4
Synthesis of the Iodonium Salt

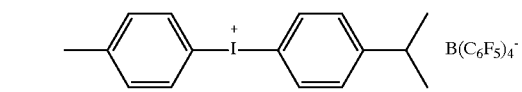

Potassium tetrakis(pentafluorophenyl)borate (18 g, 0.025 mol), cumyltolyliodonium chloride (9.31 g, 0.025 mol) and methanol (110 g) are placed in a 100 ml conical flask fitted with a magnetic stirrer. This mixture is stirred for 2 h at room temperature and then filtered through a No. 4 sinter funnel to remove the potassium chloride formed during the reaction. The solution is taken up in a conical flask fitted with a magnetic stirrer and water (150 ml) is then added dropwise over 20 min. The mixture is then kept stirring for 30 min. It is filtered through a No. 4 sinter funnel and the product obtained is then washed with 3 fractions of water (3×100 ml) and is then dried for 24 h at 50° C. under a pressure of 20 mm Hg. 15.6 g of a white powder are recovered, equivalent to a yield of 61%.

Analyses: HPLC: Anion 56.9%, cation 40.5.

Example 5
Synthesis of the Anion: $KB(PhOCF_3)_4$

Isopropyl ether (200 ml) and 4-bromotri fluorcanisole (51.6 g; 214.2 mmol) are placed in a jacketed 600 ml reactor fitted with a mechanical stirrer, a condenser containing cardice and acetone, and a dropping funnel. The assembly is placed under vigorously inert conditions with argon, and hexyllithium at a concentration of 33% in hexane (56.8 g, 203 mmol) is placed in the dropping funnel under inert atmosphere. The reaction mixture is cooled to a temperature of −70° C. by circulation of a cardice-acetone mixture in the jacket. The hexyllithium is then added dropwise over 20 min. The reaction mass turns orange. The dropping funnel is replaced with a new dropping funnel containing boron trichloride as a 1M solution in heptane (34.1 g, 46.1 mmol). The addition lasts 15 min and the reactor jacket is then emptied and the reaction mass is allowed to warm up. At a temperature of 0° C., saturated aqueous potassium chloride solution (200 ml) is poured onto the reaction mass. The mixture is stirred for 15 min and stirring is then stopped and the phases are separated. 250 ml of saturated aqueous KCl solution are added to the organic phase and the organic products are then distilled under reduced pressure (100 mm Hg) up to the boiling point of water. During the distillation, the potassium tetrakis(trifluoroanisyl)borate precipitates. It is collected, after cooling the reaction mass, by filtration. The white solid obtained is dried for 24 h at a temperature of 50° C. under a vacuum of 20 mm Hg. 26.8 g of product are recovered, i.e. a yield of 84%.

Analyses: m.p.:>300° C. (dec.); $^1$H NMR (300 MHz): purity 95% (mol); $^{19}$F NMR (282 MHz): δ=19.97.

Example 6
Synthesis of the Iodonium Salt

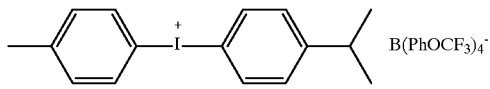

Potassium tetrakis(trifluoroanisyl)borate (7.14 g, 0.020 mol), cumyltolyliodonium chloride (3.83 g, 0.020 mol) and methanol (40 g) are placed in a 100 ml conical flask fitted with a magnetic stirrer. This mixture is stirred for 2 h at room temperature and is then filtered through a No. 4 sinter funnel to remove the potassium chloride formed during the reaction. The solution is taken up in a conical flask fitted with a magnetic stirrer and is then poured into a stock of water (300 ml). Saturated aqueous potassium chloride solution (100 ml) is then added to flocculate the white solid. This mixture is filtered through a No. 4 sinter funnel and the product obtained is then washed with 1 fraction of water (500 ml) and then dried for 24 h at 50° C. under a pressure of 20 mm Hg. 8.4 g of a white powder are recovered, equivalent to a yield of 83%.

Analyses: HPLC: Anion 64.2%, cation 30.4%.

Example 7
Synthesis of the Iodonium Salt

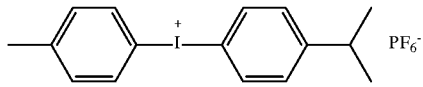

Sodium hexafluorophosphate (6.7 g, 0.040 mol), cumyltolyliodonium chloride (14.9 g, 0.040 mol) and methanol (80 g) are placed in a 100 ml conical flask fitted with a magnetic stirrer. This mixture is stirred for 1 h at room temperature and is then filtered through a No. 4 sinter funnel to remove the sodium chloride formed during the reaction. The solution is taken up in a conical flask fitted with a magnetic stirrer and is then poured onto a stock of water (600 ml). Saturated aqueous potassium chloride solution (50 ml) is then added to flocculate the white solid. This mixture is filtered through a No. 4 sinter and the product obtained is then washed with 3 fractions of water (100 ml) and then dried for 24 h at 45° C. under a pressure of 20 mm Hg. 14.4 g of a light brown powder are recovered, equivalent to a yield of 75%.

Example 8
Synthesis of the Iodonium Salt

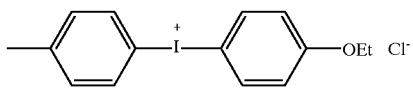

Ice (6.33 g) and sulphuric acid (21.1 g, 0.2 mol) are placed in a 500 ml four-necked flask fitted with a mechanical stirrer, a dropping funnel, a water-cooled condenser and a thermometer. The mixture is cooled to 20° C. and glacial acetic acid (30 g, 0.5 mol) is then added. Ammonium persulphate (42 g, 0.184 mol) is then added at 20° C.±5° C. The reaction mixture is then cooled to 15° C. and stirred at a speed of 420 rpm. Finally, a mixture of 4-iodotoluene (21.9 g; 0.1 mol) in ethoxybenzene (24.45 g; 0.2 mol) is added over 2 hours, while keeping the temperature at 20° C.

After addition of all the reagents, stirring is continued at 20° C. for 16 to 20 hours, the end of the reaction being determined by TLC (eluent: CCl$_4$). Precipitation of the phenethyltolyliodonium chloride is carried out by addition of an NaCl solution (35 g in 100 ml of water). The mixture is filtered and the yellow precipitate is washed with saturated NaCl solution and then with water in order to remove the remaining acetic acid. The solid is then washed with toluene, and then pentane. After drying in an oven under vacuum, the phenethyltolyliodonium chloride is recovered. It is then purified by recrystallization from hot acetone. The yield is 56%.

Analyses: m.p. =212.8° C.; $^1$H NMR (300 MHz): δ=1.14 (t, 3H, Me); 2.05 (s, 3H, Me); δ=3.77 (q, 2H, CH2); 6.85 (d, 2H, ArH); δ=7.03 (d, 2H, ArH); 8.04 (d, 2H, ArH); 8.07 (d, 2H, ArH).

Example 9
Synthesis of the Iodonium Salt

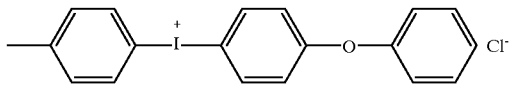

Ice, sulphuric acid and ammonium persulphate are placed in a 500 ml four-necked flask in the same manner as in Example 2. The mixture is cooled to 15° C. and stirred at 420 rpm, and a solution of 4-iodotoluene (22 g; 0.1 mol) and diphenyl ether (17.2 g; 0.05 mol) in acetic acid (32 ml) is then added over 2 hours at a temperature of 20° C. Once the reaction is complete, an NaCl solution (35 g in 100 g of water) is added. The product is recovered by filtration and is in the form of a red paste which solidifies on drying. This solid is washed thoroughly with saturated sodium chloride solution and is then taken up in hot acetone. After cooling the acetone, the product is recovered by filtration. 32.7 g of a pale yellow solid are thus recovered, equivalent to a yield of 80%.

Analyses: m.p.=189.1° C.; $^1$H NMR (300 MHz): δ=2.25 (s, 3H, Me); 6.91 (d, 2H, ArH); δ=7.01 (d, 2H, ArH); 6.85 (d, 2H, ArH); δ=7.16 (t, 1H, ArH); 7.20 (d, 2H, ArH); 7.37 (dd, 2H, ArH); 7.94 (d, 2H, ArH); 8.02 (d, 2H, ArH).

Example 10
Synthesis of the Iodonium Salt

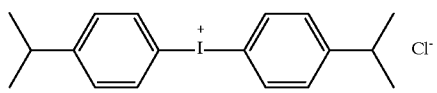

The iodonium salt 10 is prepared according to the process described in Example 1 for ditolyliodonium chloride, replacing the iodotoluene with iodocumene and the toluene with cumene. The iodonium salt is obtained in a yield of 48%.

Analyses: m.p.=176.5° C.; $^1$H NMR (300 MHz): δ=1.14 (d, 12H, Me); 2.88 (m, 2H, CH); 7.32 (d, 4H, ArH); 8.05 (d, 4H, ArH).

Example 11
Synthesis of the Iodonium Salt

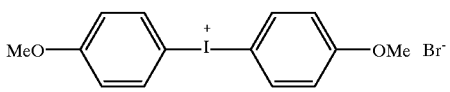

The iodonium salt 11 is prepared according to the process described in Example 1 for ditolyliodonium chloride, replacing the iodotoluene with iodoanisole and the toluene with anisole. The expected product is obtained in a yield of 30%.

Example 12
Synthesis of the Iodonium Salt

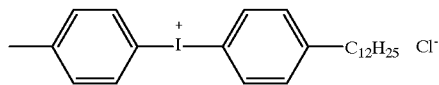

The iodonium salt 12 is prepared according to the process described in Example 1 for ditolyliodonium chloride, replacing the toluene with dodecylbenzene. The expected product is obtained in a yield of 55%.

Analyses: m.p.=132° C.; $^1$H NMR (300 MHz): δ=0.85 (t, 3H, Me); 1.22 (m, CH$_2$); 1.44 (m, CH$_2$); 2.08 (s, 3H, Me); 2.47 (t, 2H, CH$_2$); 7.04 (d, 2H, ArH); 7.19 (d, 2H, ArH); 8.11 (d, 2H, ArH); 8.20 (d, 2H, ArH).

II. Toxicology Tests on the Initiators

The following toxicology tests were carried out:

Ames test: this Ames test makes it possible to measure the mutagenic power of the product LLNA sensitization test: this test makes it possible to detect the sensitizing power of the product. The cytotoxicity of the products can also be detected in the course of the test.

Table I below indicates the results obtained for the various photoinitiators prepared above.

The tests made it possible to determine the photoinitiator structures corresponding negatively to the Ames test and negatively to the LLNA sensitizing test.

In the context of the tests, all the non-toxic photoinitiators are characterized by the presence of the following asymmetric structure:

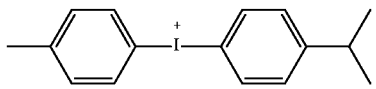

The other photoinitiators tested are positive in the LLNA sensitization test, and/or positive in the Ames test and/or possibly cytotoxic.

TABLE I

| No. | cation structure | anion | LLNA sensit. | Ames |
|---|---|---|---|---|
| 3 | | Cl$^-$ | negative | negative |
| 4 | | B(C$_6$F$_5$)$_4^-$ | negative | negative |
| 6 | | B(PhOCF$_3$)$_4^-$ | negative | negative |
| 7 | | PF$_6^-$ | negative | negative |

TABLE I-continued

| cation No. structure | anion | LLNA sensit. | Ames |
|---|---|---|---|
| 1 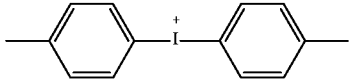 | Cl⁻ | cytotoxic | cytotoxic |
| 11 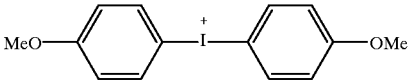 | Br⁻ | cytotoxic | cytotoxic |
| 8 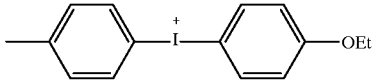 | Cl⁻ | positive | positive and cytotoxic |
| 12 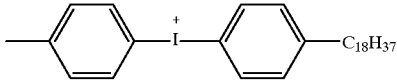 | Cl⁻ | cytotoxic | cytotoxic |
| 9 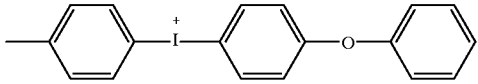 | Cl⁻ | negative | cytotoxic |
| 10 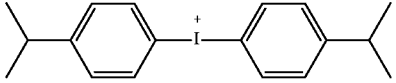 | Cl⁻ | positive | negative |
| 2 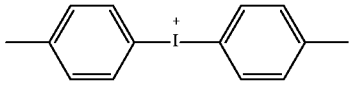 | B(C₆F₅)₄⁻ | positive | positive |

III. Preparation of Crosslinkable Resins Comprising Silicone Polymers

Resins in accordance with the invention, comprising silicone polymers (epoxysilicone matrix) were prepared.

The crosslinkable compositions comprise the non-toxic initiator prepared in Example 4. The photoinitiator of Example 4, like those of Examples 3, 6 and 7, has a reactivity under UV irradiation which is comparable with that of the other toxic photo-initiators.

A. Preparation of the crosslinkable composition

The following are mixed together;

100 parts by weight of the functionalized polyorganosiloxane used in the present preparation is (1,2-epoxy-4-ethylcyclo-hexyl) polydimethylsiloxane of formula below, in which a and b have average values of 7 and 73, respectively.

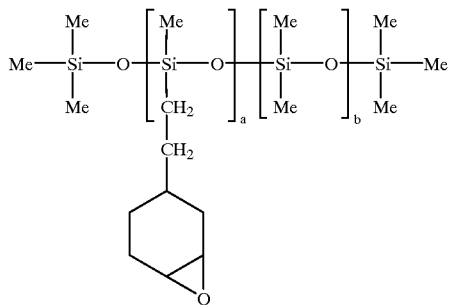

and 0.5 part by weight of initiator prepared in Example 4 dissolved to a proportion of 20% by weight in 4-hydroxy-4-methyl-2-pentanone.

B. Evaluation of non-stick coating based on crosslinked resins

After stirring for 30 minutes, the crosslinkable composition is deposited (about 0.5 to 3 g/m³) on a PEK 40/12 polyethylene layered paper sold by the company Lonjan.

The coated paper passes under a UV lamp of Fusion System F450 technology, characterized by:
- a wavelength of 360 nm,
- an absence of electrodes,
- a power of 120 W/cm irradiated.

The throughput speed of the paper under the lamp is 200 m/min.

After passage under the lamp, the quality of the coating obtained after curing is evaluated by measuring the non-stick properties of the silicone layer after it has been placed in contact:
  (i) with an acrylic adhesive TESA 4970
    for 20 hours at 23° C.,
    for 20 hours at 70° C.,
    for 7 days at 70° C.
  (ii) with a rubber adhesive TESA 4154 for 20 hours and 15 days at 23° C.
  (iii) with a rubber adhesive TESA 4651 for 20 hours and 15 days at 23° C.

The results obtained are given in Table II. The coatings obtained show extremely stable adhesion forces, even after accelerated ageing by increasing the temperature.

Moreover, the content of extractable organosilicone product is measured, after extraction for 24 hours in toluene. Only 2.2% of silicone is found in the toluene phase, which reveals good crosslinking of the resin.

TABLE II

|  | TESA 4154 | TESA 4651 | TESA 4970 |
|---|---|---|---|
| 20 h/23° C. | 2.2 g/cm | 6.2 g/cm | 6.9 g/cm |
| 15 days/23° C. | 2.7 g/cm | 6.8 g/cm | 8.2 g/cm |
| 20 h/70° C. | / | / | 9.0 g/cm |
| 7 days/70° C. | / | / | 13.7 g/cm |

IV. Preparation of Resins Based on Crosslinkable Compositions for the Manufacture of White Inks The crosslinkable compositions tested comprise either the photoinitiator P1 or the photoinitiator P2. The resins with P1 or P2 are compared with the resins crosslinked in the presence of the photoinitiator P3 from the company Sartomer.

(P1)

(P2)

(P3)

A. Preparation of the Crosslinkable Compositions

1. A concentrated base pigment (CBP) is obtained in a 2-liter reactor fitted with a three-blade central stirrer, by dispersing:
   700 parts of titanium oxide of rutile type, sold by the company Dupont de Nemours,
   3.5 parts of dispersant Solsperse 24,000 C sold by the company Zeneca, and
   296.5 parts of cycloaliphatic epoxy resin M1 sold under the name Cyracure 6110 or 6105 by Union Carbide:

(M1)

This concentrated pigment base is obtained by mixing for 30 minutes after addition of the titanium oxide powder to the resin/dispersant mixture preheated to 40° C. The concentrated pigment base is then formulated with the photoinitiator and the additives such as levelling agents (BYK361 for example) or a flexibilizing agent such as the product T1 sold by Union Carbide:

(T1)

2. Before being added to the pigment base, the photoinitiators are dissolved in the presence of the photosensitizer belonging to the thioxanthone family. In the present case, 1-chloro-4-propoxythidxanthone (CPTX) is used. The solutions are prepared by mixing at 20° C. with isopropanol and vinyl ether DVE-3 sold by the company ISP, of formula:

This vinyl ether allows very good dilution of the compounds and very good stability of the solutions stored under protection from light.

The mixing is carried out by magnetic stirring for one hour under protection from light. Clear solutions are obtained, which are stored under protection from light.

Table III indicates the parts of each constituent in the isopropanol and vinyl ether solutions S1 to S9.

TABLE III

| Reagents | S1 | S2 | S3 | S4 | S5 | S6 | S7 | S8 | S9 |
|---|---|---|---|---|---|---|---|---|---|
| DVE-3 (parts) | 12 | 12 | 12 | 12 | 12 | 12 | 12 | 12 | 12 |
| P1 | 4 | 0 | 0 | 4 | 0 | 0 | 4 | 0 | 0 |
| P2 | 0 | 4 | 0 | 0 | 4 | 0 | 0 | 4 | 0 |
| P3 | 0 | 0 | 4 | 0 | 0 | 4 | 0 | 0 | 4 |
| Isopropanol | 4 | 4 | 4 | 4 | 4 | 4 | 4 | 4 | 4 |
| CPTX | 1.2 | 1.2 | 1.2 | 1.6 | 1.6 | 1.6 | 1.92 | 1.92 | 1.92 |

3. These solutions S1 to S9 are then mixed with the concentrated pigment base. The percentages of the constituents of the crosslinkable compositions F1 to F9 are given in Table IV below.

TABLE IV

| Reference | F1 | F2 | F3 | F4 | F5 | F6 | F7 | F8 | F9 |
|---|---|---|---|---|---|---|---|---|---|
| CPB % | 81.7 | 81.7 | 81.7 | 81.7 | 81.7 | 81.7 | 81.7 | 81.7 | 81.7 |
| S1 % | 10.6 | 0 | 0 | 0 | 0 | 0 | 0 | 0 | 0 |
| S2 % | 0 | 10.6 | 0 | 0 | 0 | 0 | 0 | 0 | 0 |
| S3 % | 0 | 0 | 10.6 | 0 | 0 | 0 | 0 | 0 | 0 |
| S4 % | 0 | 0 | 0 | 8.1 | 0 | 0 | 0 | 0 | 0 |
| S5 % | 0 | 0 | 0 | 0 | 8.1 | 0 | 0 | 0 | 0 |
| S6 % | 0 | 0 | 0 | 0 | 0 | 8.1 | 0 | 0 | 0 |
| S7 % | 0 | 0 | 0 | 0 | 0 | 0 | 6.85 | 0 | 0 |
| S8 % | 0 | 0 | 0 | 0 | 0 | 0 | 0 | 6.85 | 0 |
| S9 % | 0 | 0 | 0 | 0 | 0 | 0 | 0 | 0 | 6.85 |
| M1 % | 2.2 | 2.2 | 2.2 | 4.7 | 4.7 | 4.7 | 5.95 | 5.95 | 5.95 |
| T1 % | 4 | 4 | 4 | 4 | 4 | 4 | 4 | 4 | 4 |
| BYK361 % | 1.5 | 1.5 | 1.5 | 1.5 | 1.5 | 1.5 | 1.5 | 1.5 | 1.5 |

Evaluation of the Inks Obtained Based on the Linked Resins of F1 to F9

The drying of the inks is evaluated on a UV machine from the company IST GmbH fitted with a mercury lamp and a gallium-doped mercury lamp. The lamps have a power rating of 180 W/cm and are calibrated using a Powerpuck cell from the company E.I.T., so as to determine the intensity and dose received as a funciton of the throughput speed of the machine.

At a throughput speed of 10 m/min, each formulation receives:
UVA (320–390 nm)=0.641 J/cm$^2$; UvB (280–320 nm)=0.564 J/cm$^2$;
UVC (250–260 nm)=0.078 J/cm$^2$; and UVV (390–440 nm)=0.1255 J/cm$^2$ At a throughput speed of 20 m/min, each formulation receives:
UVA (320–390 nm)=0.314 J/cm$^2$; UVB (280–320 nm)=0.276 J/cm$^2$;
UVC (250–260 nm)=0.033 J/cm$^2$; and UVV (390–440 nm)=0.781 J/cm$^2$ At a throughput speed of 50 m/min, each formulation receives:
UVA (320–390 nm)=0.100 J/cm$^2$; UVB (280–320 nm)=0.092 J/cm$^2$;
UVC (250–260 nm)=0.012 J/cm$^2$; and UVV (390–440 nm)=0.599 J/cm$^2$.

(i) The resistance to solvents of the inks obtained after drying 12 μm±3 μm films on aluminium support by means of the number of to-and-fro motions made using a cloth soaked with solvent, this number being the value required to deaggregate the layer of ink after 1 hour and after 24 hours. In the present case, the solvent used is methyl ethyl ketone (MEK).

(ii) The flexibility of the layers is also measured according to the T-Bend method. The plate, 250 μm thick, is folded on itself. If no lifting of the layer of ink is noted after stripping with cellotape on the strip, a grade T0is recorded. If the coating cracks or tears and/or is stripped off by the cellotape, the plate is folded a second time and the same observations are made. If the coating is not affected by this second folding, it is recorded that the product corresponds to T0.5, the value corresponding to the ratio of the radius of curvature to the thickness. If the test is negative, the process is continued up to T3, i.e. a radius of curvature equal to three times the thickness. Beyond this point, it is considered that the layer of ink is fragile and relatively inflexible.

(iii) The adhesion, graded from 0 to 5, is also measured according to standardized "crosshatch adhesion" method. 0=100% adhesion.

The results of the evaluations are given in Table V below.

TABLE V

| Speed; | 10 m/mn | 10 m/mn | 10 m/mn | 10 m/mn | 10 m/mn | 10 m/mn | 10 m/mn | 10 m/mn | 10 m/mn |
|---|---|---|---|---|---|---|---|---|---|
| formulation | F1 | F2 | F3 | F4 | F5 | F6 | F7 | F8 | F9 |
| Crosslinking | 1 pass | 1 pass | 1 pass | 1 pass | 1 pass | 1 pass | 1 pass | 1 pass | >1 pass |
| MEK(24 h) | 95 | >100 | >100 | 9 | >100 | >100 | 23 | 42 | / |
| Adhesion | 0 | 0 | 0 | 0 | 0 | 0 | 0 | 0 | / |
| T bend | T3 | >T3 | >T3 | T1.5 | T2 | T2 | T1.5 | T2 | / |
| Speed; | 20 m/mn | 20 m/mn | 20 m/mn | 20 m/mn | 20 m/mn | 20 m/mn | 20 m/mn | 20 m/mn | 20 m/mn |
| formulation | F1 | F2 | F3 | F4 | F5 | F6 | F7 | F8 | F9 |
| Crosslinking | 1 pass | 1 pass | 1 pass | 1 pass | 1 pass | 1 pass | >1 pass | >1 pass | >1 pass |
| MEK(24 h) | 20 | 100 | >100 | 7 | 90 | 30 | / | / | / |
| Adhesion | 0 | 0 | 0 | 0 | 0 | 0 | / | / | / |
| T bend | T3 | T3 | >T3 | T1.5 | T>3 | T3 | / | / | / |
| Speed; | 50 m/mn | 50 m/mn | 50 m/mn | 50 m/mn | 50 m/mn | 50 m/mn | 50 m/mn | 50 m/mn | 50 m/mn |
| formulation | F1 | F2 | F3 | F4 | F5 | F6 | F7 | F8 | F9 |
| Crosslinking | 1 pass | 1 pass | 1 pass | >1 pass | 1 pass | 1 pass | >1 pass | >1 pass | >1 pass |
| MEK(24 h) | 5 | 90 | 100 | / | 20 | 0 | / | / | / |
| Adhesion | 0 | 0 | 0 | / | 0 | 3 | / | / | / |
| T bend | T2 | T2 | T2.5 | / | T2 | >T3 | / | / | / |

What is claimed is:

1. A process for preparing a non-toxic resin from a composition comprising a monomer, oligomer and/or polymer, wherein said monomer, oligomer and/or polymer contains organofunctional groups and can be crosslinked under irradiation in the presence of an initiator system, wherein the initiator system is an onium salt whose cationic structure is of the formula:

$$[(CH(CH_3)_2\text{-}\phi\text{-})\text{-}I\text{---}(\text{---}R^1)]^+ \quad (I)$$

in which the symbol $R^1$ represents a radical $-\phi-R^2$, $R^2$ being a linear or branched alkyl radical comprising from 1 to 10 carbon atoms, and $\phi$ represents a phenyl group, said process comprising the following steps:
  a) mixing molecules of said monomer, oligomer and/or polymer with said initiator system to obtain a mixture; and
  b) irradiating the mixture to obtain said non-toxic resin.

2. Preparation process according to claim 1, wherein the cationic structure of the onium salt is of the formula $$[(CH(CH_3)_2\text{-}\Phi\text{-})\text{-}I\text{-}\Phi\text{-}CH_3]^+.$$

3. Preparation process according to claim 1, wherein the initiator is an onium salt in which the anionic structure is chosen from the group consisting of $Cl^-$, $Br^-$, $BF_4^-$, $PF_6^-$, $CF_3SO_3^-$, $N(SO_2CF_3)_2^-$, $C(SO_2CF_3)_2^-$, $B(C_6F_5)_4^-$, $B(PhOCF_3)_4^-$, $SbF_6^-$ and/or $AsF_6^-$.

4. A process according to claim 1, wherein the initiator is an onium salt selected from the group consisting of
  $[CH_3\text{---}\phi\text{---}I\text{---}\phi\text{---}CH(CH_3)_2]^+Cl^-$,
  $[CH_3\text{---}\phi\text{---}I\text{---}\phi\text{---}CH(CH_3)_2]^+PF_6^-$,
  $[CH_3\text{---}\phi\text{---}I\text{---}\phi\text{---}CH(CH_3)_2]^+B(C_6F_5)_4^-$, and
  $[CH_3\text{---}\phi\text{---}I\text{---}\phi\text{---}CH(CH_3)_2]^+B(PhOCF_3)_4^-$.

5. Preparation process according to claim 1, wherein the crosslinking is carried out under ultraviolet irradiation and/or under irradiation with an electron beam.

6. A process according to claim 1, wherein said monomer, oligomer and/or polymer is
  a polyorganosiloxane consisting of units of formula (II) ending with units of formula (III), or
  a cyclic polyorganosiloxane consisting of units of formula (II),
wherein formulae (II) and (III) are represented below:

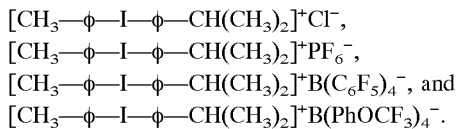

in which
  the symbols $R_3$ are identical or different and represent:
    a linear or branched alkyl radical containing 1 to 8 carbon atoms, optionally substituted with at least one halogen,
    a cycloalkyl radical containing between 5 and 8 carbon ring atoms optionally substituted,
    a aryl radical containing between 6 and 12 carbon atoms which may be substituted,
    an aralkyl radical with an allyl portion containing between 5 and 14 carbon atoms and an aryl portion containing between 6 and 12 carbon atoms, optionally substituted on the aryl portion with halogens, alkyls and/or alkoxys containing 1 to 3 carbon atoms, and
  the symbols Y are identical or different and represent: the group $R_3$, a hydrogen atom and/or an organofunctional group which can undergo cationic crosslinking, and at least one of the symbols Y representing an organofunctional group which can undergo cationic crosslinking.

7. Preparation process according to claim 6, wherein at least one of the symbols $R_3$ of the polyorganosiloxanes used represents a phenyl, tolyl or dichlorophenyl radical.

8. A process according to claim 6,
  wherein in the symbol $R_3$ said halogen is fluorine, said alkyl radical is methyl, ethyl, propyl, octyl or 3,3,3-trifluoropropyl, said aryl radical is phenyl, and said aryl radical that may be substituted is diclorophenyl; and
  wherein in the symbol Y said organofunctional group is a epoxyfunctional group or vinyloxyfunctional group linked to a silicon atom of the polyorganosiloxane or cyclic polyorganosiloxane.

9. A process according to claim 1, wherein said organofunctional groups are selected from the group consisting of epoxy reactive functions, acrylate reactive functions, alkenyl ether reactive functions, alcohol reactive functions and mixtures thereof.

10. A process according to claim 9, wherein said monomer, oligomer and/or polymer is selected from the group consisting of a cycloaliphatic epoxide, non-cycloaliphatic epoxide, acrylate, linear or cyclic alkenyl ether, polyol and mixtures thereof.

11. A process according to claim 10, wherein
  said cycloaliphatic epoxide is an epoxide of cyclohexylmethyl epoxycyclohexane carboxylate or bis(3,4-epoxycyclohexyl) adipate;
  said non-cycloaliphatic epoxide is an α-olefin epoxide, Novolac epoxide, epoxidized soybean oil, epoxidized flax oil, epoxidized polybutadiene, or epoxide resulting from the coupling of bisphenol A and epichlorohydrin;
  said acrylate is an epoxidized acrylate, acrylo-glyceropolyester, multifunctional acrylate, acrylo-urethane, acrylo-polyether, acrylo-polyester, unsaturated polyester or acrylo-acrylic; and
  said linear or cyclic alkenyl ether is a vinyl ether, cyclic vinyl ether, acrolein tetramer, acrolein dimer or propenyl ether.

12. A process according to claim 9, wherein said monomer, oligomer and/or polymer is
  a polyorganosiloxane consisting of units of formula (II) ending with units of formula (III), or
  a cyclic polyorganosiloxane consisting of units of formula (II), wherein formulae (II) and (III) are represented below:

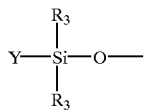
(III)

in which
the symbols $R_3$ are identical or different and represent:
a linear or branched alkyl radical containing 1 to 8 carbon atoms, optionally substituted with at least one halogen,
a cycloalkyl radical containing between 5 and 8 carbon ring atoms optionally substituted,
an aryl radical containing between 6 and 12 carbon atoms which may be substituted, or
an aralkyl radical with an alkyl portion containing between 5 and 14 carbon atoms and an aryl portion containing between 6 and 12 carbon atoms, optionally substituted on the aryl portion with halogens, alkyls and/or alkoxys containing 1 to 3 carbon atoms, and the symbols Y are identical or different and represent:
the group $R_3$, a hydrogen atom and/or an organofunctional group which can undergo cationic crosslinking, and at least one of the symbols Y representing an organofunctional group which can undergo cationic crosslinking.

13. A process according to claim 12,
wherein in the symbol $R_3$ said halogen is fluorine, said alkyl radical is methyl, ethyl, propyl, octyl or 3,3,3-trifluoropropyl, said aryl radical is phenyl, and said aryl radical that may be substituted is diclorophenyl; and
wherein in the symbol Y said organofunctional group is a epoxyfunctional group or vinyloxyfunctional group linked to a silicon atom of the polyorganosiloxane or cyclic polyorganosiloxane.

14. Resin which is obtained from the preparation process according to claim 1.

15. Non-toxic, non-stick coating comprising a resin according to claim 11.

16. Non-toxic ink based on resin according to claim 11.

17. An article comprising at least one surface coated with a resin prepared with a process according to claim 1, wherein said monomer, oligomer and/or polymer is of an organic nature and/or silicone nature,
wherein said monomer, oligomer and/or polymer of an organic nature is an organic monomer, oligomer and/or polymer comprising epoxy, acrylate, alkenyl ether and/or alcohol reactive functions, and
wherein said monomer, oligomer and/or polymer of silicone nature is a monomer, oligomer and/or polymer which can form a silicone.

18. An article according to claim 17, wherein said monomer, oligomer and/or polymer of an organic nature is selected from the group consisting of a cycloaliphatic epoxide, non-cycloaliphatic epoxide, acrylate, linear or cyclic alkenyl ether, polyol and mixtures thereof.

19. A non-toxic ink or coating comprising a resin according to claim 11.

20. The coating and/or ink according to claim 19 which is intended for food use.

21. A non-toxic initiator system for the preparation of a crosslinkable composition, comprising an onium salt wherein the cationic structure of the onium salt is of the formula:

(I)

in which the symbol $R^1$ represents a radical $-\phi-R^2$, $R^2$ being a linear or branched alkyl radical comprising from 1 to 20 carbon atoms.

22. The non-toxic initiator system according to claim 21, wherein the cationic structure of the onium salt is of the formula:

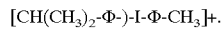

23. The non-toxic initiator system according to claim 17, wherein the crosslinkable composition is prepared for the purpose of manufacturing non-stick, non-toxic coatings.

24. The non-toxic initiator system according to claim 22, wherein the non-toxic, non-stick coatings are for food use.

* * * * *